US010071214B2

(12) United States Patent
Mansfield et al.

(10) Patent No.: US 10,071,214 B2
(45) Date of Patent: Sep. 11, 2018

(54) LEAK DETECTION SYSTEM AND METHOD FOR TUBE OR CATHETER PLACEMENT

(71) Applicant: SONARMED INC., Carmel, IN (US)

(72) Inventors: Jeffrey P. Mansfield, Carmel, IN (US); Andrew D. Cothrel, Carmel, IN (US); Laura L. Lyons, Carmel, IN (US)

(73) Assignee: SONARMED INC., Carmel, IN (US)

( * ) Notice: Subject to any disclaimer, the term of this patent is extended or adjusted under 35 U.S.C. 154(b) by 22 days.

(21) Appl. No.: 15/336,186

(22) Filed: Oct. 27, 2016

(65) Prior Publication Data

US 2017/0043110 A1 Feb. 16, 2017

Related U.S. Application Data

(62) Division of application No. 13/783,916, filed on Mar. 4, 2013, now Pat. No. 9,498,590.

(60) Provisional application No. 61/606,679, filed on Mar. 5, 2012.

(51) Int. Cl.
| | |
|---|---|
| *A61M 16/00* | (2006.01) |
| *A61M 16/04* | (2006.01) |
| *A61M 5/50* | (2006.01) |
| *A61M 5/168* | (2006.01) |
| *A61M 25/10* | (2013.01) |

(52) U.S. Cl.
CPC ...... *A61M 16/044* (2013.01); *A61M 5/16831* (2013.01); *A61M 5/5086* (2013.01); *A61M 16/0003* (2014.02); *A61M 16/0006* (2014.02); *A61M 16/0051* (2013.01); *A61M 16/021* (2017.08); *A61M 25/10184* (2013.11); *A61M 25/10188* (2013.11); *A61M 2016/0027* (2013.01); *A61M 2205/15* (2013.01); *A61M 2205/3375* (2013.01); *A61M 2205/502* (2013.01); *A61M 2205/581* (2013.01)

(58) Field of Classification Search
CPC ............... A61M 5/50; A61M 2205/15; A61M 2016/206; A61M 2205/32; A61M 2205/3368; A61M 2205/3375; A61M 2230/205; A61M 5/16831; A61M 5/5086; A61B 5/14542; A61B 5/1459; A61B 5/4233
USPC .......... 128/202.22, 207.15, 207.14; 600/437; 181/126, 70, 139
See application file for complete search history.

(56) References Cited

U.S. PATENT DOCUMENTS

| | | |
|---|---|---|
| 4,501,273 A | 2/1985 | McGinnis |
| 4,630,606 A | 12/1986 | Weerda |
| 4,697,593 A | 10/1987 | Evans |
| 5,445,144 A | 8/1995 | Wodicka |
| 5,575,310 A | 11/1996 | Kamen |
| 5,655,518 A | 8/1997 | Burden |

(Continued)

*Primary Examiner* — Kari Rodriquez
*Assistant Examiner* — Victoria Murphy
(74) *Attorney, Agent, or Firm* — Wilson Sonsini Goodrich & Rosati

(57) ABSTRACT

The present disclosure relates to a leak detection system and method for tube or catheter placement. The system and method includes acoustically sensing a leak in the seal between a tube or catheter within a body and the body cavity against which it is sealed, assisting the user in adjusting the system until the leak has been substantially sealed, and establishing system parameters to be used thereafter to maintain the system in an operating state that will substantially prevent leakage, all using a noninvasive acoustic technique.

20 Claims, 5 Drawing Sheets

(56) References Cited

U.S. PATENT DOCUMENTS

| | | |
|---|---|---|
| 5,853,005 A | 12/1998 | Scanlon |
| 6,629,527 B1 | 10/2003 | Estes |
| 6,705,319 B1 | 3/2004 | Wodicka |
| 7,891,354 B2 | 2/2011 | Farbarik |
| 8,038,629 B2 | 10/2011 | Solanki |
| 8,152,751 B2 | 4/2012 | Roger |
| 8,280,489 B2 | 10/2012 | Li |
| 8,371,303 B2 | 2/2013 | Schaner |
| 8,394,031 B2 | 3/2013 | Mansy |
| 8,424,529 B2 | 4/2013 | Efrati |
| 8,522,787 B2 | 9/2013 | Lin |
| 8,608,658 B2 | 12/2013 | Burbank |
| 8,611,984 B2 | 12/2013 | Greenburg |
| 8,764,725 B2 | 7/2014 | Averbuch |
| 8,844,534 B2 | 9/2014 | Behlmaier |
| 8,905,029 B2 | 12/2014 | Colburn |
| 2002/0016610 A1 | 2/2002 | Hovanes |
| 2003/0034035 A1 | 2/2003 | Raphael |
| 2006/0081255 A1 | 4/2006 | Miller |
| 2006/0107962 A1 | 5/2006 | Ward |
| 2007/0137652 A1 | 6/2007 | Qureshi |
| 2007/0257788 A1 | 11/2007 | Carlson |
| 2008/0078248 A1* | 4/2008 | Farbarik ............... A61M 16/00 73/613 |
| 2009/0025728 A1 | 1/2009 | Aljuri |
| 2009/0082676 A1 | 3/2009 | Bennison |
| 2009/0229605 A1* | 9/2009 | Efrati ................ A61M 16/044 128/203.12 |
| 2009/0301601 A1 | 12/2009 | Enerson |
| 2010/0252048 A1 | 10/2010 | Young |
| 2011/0030694 A1 | 2/2011 | Schaner |
| 2011/0197888 A1 | 8/2011 | Deutsch |
| 2012/0232411 A1 | 9/2012 | Brunner |
| 2013/0098363 A1 | 4/2013 | Forte |
| 2013/0255691 A1 | 10/2013 | Mansfield |
| 2013/0281885 A1 | 10/2013 | Rowbottom |
| 2014/0051989 A1 | 2/2014 | McGowan |
| 2014/0366874 A1 | 12/2014 | Deutsch |

\* cited by examiner

FIG. 1
PRIOR ART
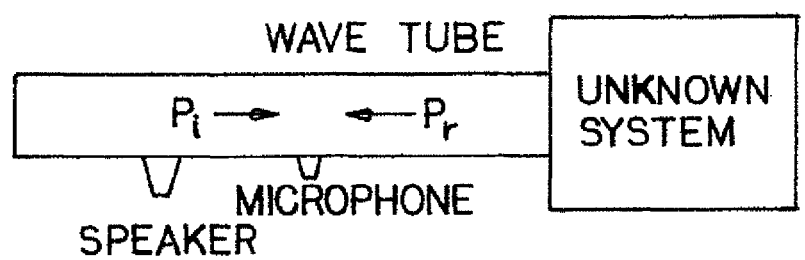
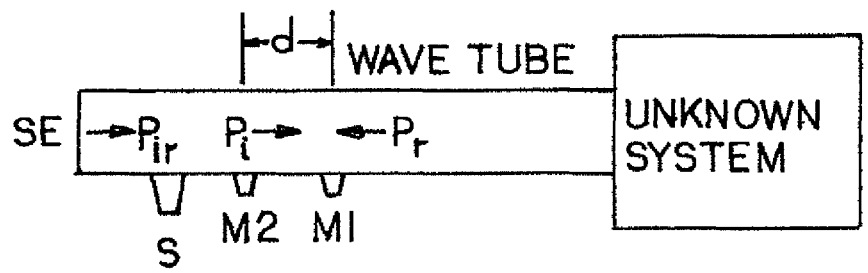
PRIOR ART
FIG. 2

LEAK DETECTION SYSTEM AND METHOD FOR TUBE OR CATHETER PLACEMENT

I. CROSS REFERENCE TO RELATED APPLICATIONS

This application is a divisional application of U.S. application Ser. No. 13/783,916, filed Mar. 4, 2013, now U.S. Pat. No. 9,498,590, issued Nov. 22, 2016, which claims the benefit of U.S. Provisional Application No. 61/606,679, filed Mar. 5, 2012, each of which are incorporated herein by reference.

II. FIELD

The present disclosure is generally related to a leak detection system and method for tube or catheter placement.

III. DESCRIPTION OF RELATED ART

Endotracheal tubes (hereinafter "ETTs"), often referred to as breathing tubes, are used to provide a conduit for mechanical ventilation of patients with respiratory or related problems. An ETT is inserted through the mouth or nose and into the trachea of a patient for several reasons: (1) to establish and maintain an open airway; (2) to permit positive pressure ventilation which cannot be done effectively by mask for more than brief periods; (3) to seal off the digestive tract from the trachea thereby preventing inspiration of forced air into the stomach; and (4) as an anesthesia delivery system.

ETTs are used extensively in the field, emergency rooms, surgical suites, and intensive care units for patients that require ventilatory assistance. During intubation, an ETT is typically inserted into the mouth, past the vocal cords, and into the trachea. The proper location of the ETT tip is roughly in the mid-trachea. However, there are at least three possible undesired placement positions that can result, either during intubation or due to a subsequent dislodgment. One of these positions is in the esophagus. Another undesired position occurs from over-advancement of the ETT past the bifurcation of the trachea (carina) and into one of the mainstem bronchi. A third is above the vocal cords in the vocal tract.

The structure of the human airways is extremely complex. At the upper end of the trachea is the larynx containing the vocal folds, and at the lower end is the first bifurcation, known as the carina. The adult trachea is approximately 1.4 to 1.6 cm in diameter and 9 to 15 cm long. The newborn trachea averages about 0.5 cm in diameter and 4 cm in length. The airways that are formed by the carina are the right primary bronchus and the left primary bronchus. The right primary bronchus is shorter, wider, and more vertical than the left primary bronchus. For this reason a majority of erroneous ETT insertions past the carina tend to follow the right primary bronchus. Continuing farther down the airways, the bronchi branch into smaller and smaller tubes. They finally terminate into alveoli, small airfilled sacs where oxygen-carbon dioxide gas exchange takes place.

Providing a correctly positioned and unobstructed endotracheal tube is a major clinical concern. Any misplacement or obstruction of an ETT can pose a threat to the patient's health. Misdirecting the ETT into the esophagus or locating the tip where there is a significant obstruction of its lumen can result in poor ventilation of the patient and eventually lead to cardiac arrest, brain damage or even death. Further, if the ETT is misplaced into a mainstem bronchus, lung rupture can occur.

In an attempt to avoid possible complications with Err use, several techniques have been developed to aid clinicians in the proper placement/location of ETTs. Guidelines for the ideal technique are as follows: (1) the technique should work as well for difficult intubations as it does for those not so difficult; (2) the technique should indicate a proper ETT tip location unequivocally; (3) esophageal intubation must always be detected; and (4) clinicians must understand the technique and how to use it. The known techniques for clinical evaluation of ETT location include direct visualization of the ETT placement, chest radiography, observation of symmetric chest movements, auscultation of breath sounds, reservoir bag compliance, the use of a video stethoscope, fiberoptic bronchoscopy, pulse oximetry, and capnometry. However, none of the listed techniques allow a health care provider to constantly monitor the precise location of an ETT within the trachea, or the degree of obstruction of its lumen.

Another challenge with placing the ETT in the trachea for ventilation is an undesirable backflow of air around the ETT, since such backflow reduces the amount of positive ventilation pressure that can be maintained in the lungs. To address this challenge, a cuff can be adapted to seal against the inner diameter of the trachea. However, as the tracheal walls move, leaks can still occur. In addition, post-placement movement of the ETT within the trachea can also cause leaks around the ETT. In some embodiments, the cuff may be inflated with a fluid (such as air) in order to form the seal. A cuff pressure that is too high can collapse the blood capillaries in the wall of the trachea and cause necrosis. A cuff pressure that is too low may provide an inadequate seal and result in both a reduction of positive ventilation pressure and an increased likelihood of fluid from the proximal side of the cuff (such as accumulated patient secretions) to leak into the lungs, raising the possibility of the patient contracting pneumonia.

Apparatuses and methods for acoustically guiding, positioning, and monitoring tubes within a body are known in the art. See, for example, U.S. Pat. Nos. 5,445,144 and 6,705,319 to Wodicka et al., incorporated herein by reference, which disclose an apparatus and method for acoustically monitoring the position of a tube within an anatomical conduit. In various embodiments, a sound pulse is introduced into a wave guide and is recorded as it passes by one or more microphones located in the wave guide wall. After propagating down the ETT, the sound pulse is emitted through the distal tip of the ETT into the airway (or wherever in the body the tip of the ETT is located) and an acoustic reflection propagates back up the BIT to the wave guide for measurement by the same microphone(s). The amplitude and the polarity of the incident and reflected sound pulse are used to estimate the characteristics of the airway and the ETT, and thereby guide the MT placement or monitor the ETT for patency.

As disclosed by Wodicka, et al., the acoustical properties of the airways of a respiratory system change dramatically over the audible frequency range. At very low frequencies, the large airway walls are yielding and significant wall motion occurs in response to intra-airway sound. In this frequency range, the airways cannot be represented accurately as rigid conduits and their overall response to sonic pulses is predictably complex. At very high audible frequencies, the large airway walls are effectively more rigid due to their inherent mass. However, one-dimensional sound propagation down each airway segment cannot be ensured as the sonic wavelengths approach in size the diameter of the segment, and effects of airway branching are thought to increase in importance. There appears to be a finite range of frequencies between roughly 500 and 6,000 Hz where the large airways behave as nearly rigid conduits and the acoustical effects of the individual branching segments are not dominant. It is over this limited frequency range where the complicated branching network can be approximately represented as a flanged "horn" and where its composite acoustical properties reflect the total cross-sectional area of the airways.

Accordingly, there is a need for an improved method and system for acoustically sensing a leak in the seal between a tube or catheter within a body and the body cavity against which it is sealed and to assist the user in adjusting the system until the leak has been substantially sealed. In addition, there is a need for establishing system parameters to be used thereafter to maintain the system in an operating state that will substantially prevent leakage, all using a noninvasive acoustic technique. However, in view of the prior art at the time the present invention was made, it was not obvious to those of ordinary skill in the pertinent art how the identified needs could be fulfilled.

IV. SUMMARY

A leak detection system and method for tube or catheter placement is disclosed. The system and method of the present disclosure conveniently utilize the microphone in the waveguide connected to the ETT to detect sounds indicative of leakage past the ETT cuff. Alternatively, another microphone independent of the microphone used to guide placement of the ETT may be used. The noninvasive system and method of the present disclosure are therefore able to assist the user in creating an adequate seal between the ETT and the trachea (or between any other tube or catheter and a body cavity into which it has been inserted) and assist in maintaining the seal once it has been established. Furthermore, the system has no moving parts, and can be easily understood and operated by skilled clinicians.

According to one aspect of the present disclosure, the system may be configured for acoustically detecting the sounds caused by fluids (such as air or other gases) leaking past a cuff sealing a tube or catheter against the walls of an anatomical conduit. Detection of these sounds, either by a human operator or by an automated system employing a processing device, can be used to warn a user of the system that a leak is occurring, and in other embodiments can automatically initiate adjustment of the system in order to stop the leak. For example, the system may include a microphone for detecting sounds in or near the tube and for generating a first signal corresponding to the detected sound, a speaker for creating an audible version of the first signal, where a user can listen to the audible version and determine if adjustments to the leakage prevention cuff are needed.

In another particular embodiment, the system may include the microphone for detecting sounds in or near the tube and for generating a first signal corresponding to the detected sound, and a processor configured to receive the first signal and to discriminate between an expected baseline representing normal sounds in or near the tube and unexpected sounds representative of leakage past the cuff, where the processor using the first signal to report that a leak has been detected. The processor may be further configured to detect that a leak is present and to then control an inflation device to automatically increase the pressure in the leak prevention cuff. In addition, the tube may be adapted to be coupled to a medical device, such as a mechanical ventilator, a breathing bag, an anesthesia machine, or an infusion pump. Further, a display may be provided in electronic communication with the processor.

In yet another illustrative embodiment, a method of acoustically detecting a leak past a cuff sealing a tube to a body is disclosed. The method includes detecting a sound in or near the tube, and audibly presenting the detected sound to a user of the tube for determination of whether a leak is present. In one aspect of this embodiment, the method further includes applying the detected sound signal to a processor that is configured to analyze the sound and detect the sound of a leak over a baseline expected sound profile. The method may also include causing the processor to operate an inflation device to renew the seal between the tube and the anatomical conduit if the processor detects a leak. In yet another aspect of this method, the detected sound may be used as a feedback mechanism when pressurizing the cuff, such that when the detected sound indicates that the leakage has stopped, the pressure of the cuff can be recorded and thereafter adjusted to maintain the pressure at that level.

Additional objects, features, and advantages of the present disclosure will become apparent to those skilled in the art upon consideration of the following detailed description of a preferred embodiment exemplifying the best mode of carrying out the teachings of the present disclosure as presently perceived.

V. BRIEF DESCRIPTION OF THE DRAWINGS

FIG. 1 is a diagrammatical view of a prior art system for determining characteristics of an unknown system;

FIG. 2 is a diagrammatical view of a prior art two-microphone system for determining characteristics of an unknown system;

VI. DETAILED DESCRIPTION

Figure 3:
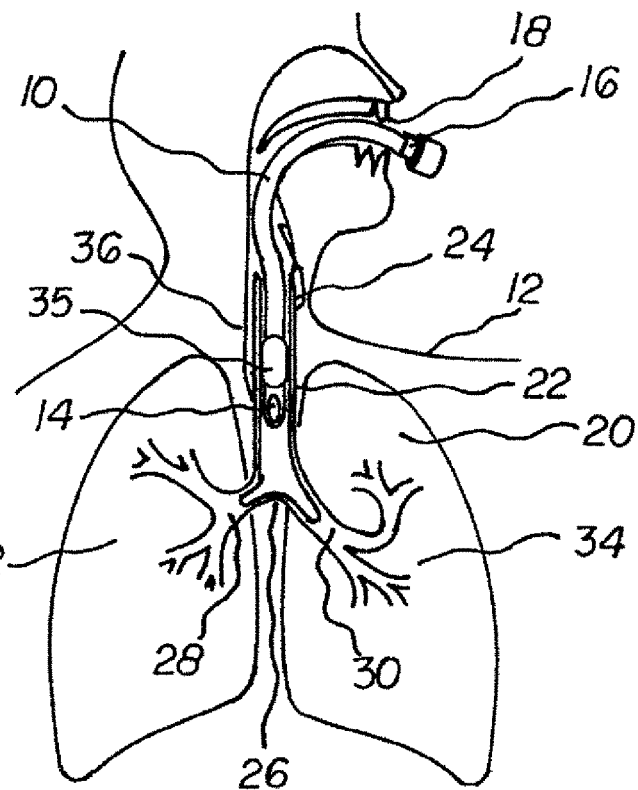
FIG. 3 is a diagrammatical view illustrating proper insertion of an endotracheal tube (ETT) into a trachea of a human body.

For purposes of promoting an understanding of the principles of the method and system, reference will now be made to the embodiment illustrated in the drawings, and specific language will be used to describe that embodiment. It will nevertheless be understood that no limitation of the scope of the method and system is intended. Alterations and modifications, and further applications of the principles of the method and system as illustrated therein, as would normally occur to one skilled in the art to which the method and system relates are contemplated, are desired to be protected. Such alternative embodiments require certain adaptations to the embodiments discussed herein that would be obvious to those skilled in the art.

When it is desired to direct an object (such as a tube, catheter, or other medical device) into an unknown system, it is known to generate a sound pulse within the tube or medical device and to receive the reflections of the pulse as they return from the unknown system, similar to the process used in sonar imaging. In the case of a system as shown in FIG. 1, a speaker transmits an incident sound pulse, $P_i$ that travels toward the unknown system. As the incident sound pulse, $P_i$, enters the unknown system, a sound pulse is reflected back, $P_r$, which can be received by the microphone. The reflected sound pulse, $P_r$, can be analyzed to determine various qualities of the unknown system, including the cross sectional area of the system. Furthermore, as the incident sound pulse $P_i$ continues to propagate through the unknown system, additional reflections may occur. These subsequent reflected sound pulses can indicate additional qualities of the unknown system, such as the depth of the system, and whether the cross sectional area changes at all throughout that depth.

A two-microphone system is shown in FIG. 2, where the two microphones are separated by a distance d. In the two-microphone system, determination can be made as to the direction of travel of a sound pulse, $P_i$ or $P_r$, by analyzing the difference between the instant in which the sound pulse is detected by the first microphone M1, and the instant in which the sound pulse is detected by the second microphone, M2. For example, if a sound pulse is first detected by M1 and then by M2, the pulse is determined to be traveling away from the unknown system, and is thus a reflected pulse $P_r$. In contrast, if a sound pulse is first detected by M2 and then M1, the pulse is determined to be traveling toward the unknown system.

The directional determination of the traveling sound pulse prevents the misreading of incident sound pulses that are reflected from the speaker end, SE, of the tube, such as $P_{ir}$. For various reasons, an incident sound pulse, $P_i$, may be reflected from the speaker end, SE, of the tube, including the presence of a blockage in the tube, a wall at the end of the tube, or the attachment of another device (i.e. a mechanical ventilator) to the end of the tube. False readings can occur when reflected sound pulse, $P_{ir}$, travels past a single microphone, such as that shown in FIG. 1. However, when two microphones are used, such as in the system illustrated in FIG. 2, a determination of the direction of travel of the reflected sound pulse, $P_{ir}$, can eliminate the possibility of a misreading.

Although the method and system described below relate to maintaining a seal between an endotracheal tube (ETT) and a portion of a respiratory system of a body, it should be understood that the system and methods of the present disclosure may be used to maintain a seal between gas or liquid filled tubes or catheters and other anatomical conduits or cavities.

As mentioned above, a method and system for guiding the positioning of an

ETT is known in the art. For a description of a single microphone system for guiding the insertion of the ETT, and a more detailed description of the analysis and theory involved in determining the position of the ETT, reference can be made to U.S. Pat. No. 5,455,144 to Wodicka, et al., previously incorporated by reference. For a description of a two-microphone system for guiding the insertion of the ETT, and a more detailed description of the analysis and theory involved in determining the position of the ETT, reference can be made to U.S. Pat. No. 6,705,319 to Wodicka, et al., previously incorporated by reference.

Figure 4:
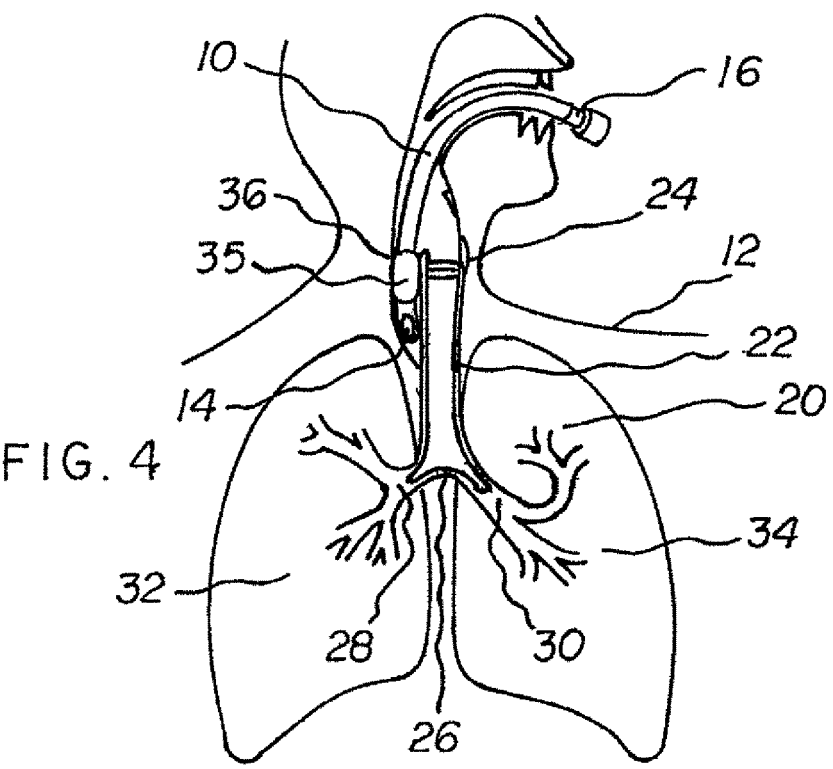
FIG. 4 is a diagrammatical view illustrating improper placement of the ETT into an esophagus.
Figure 5:
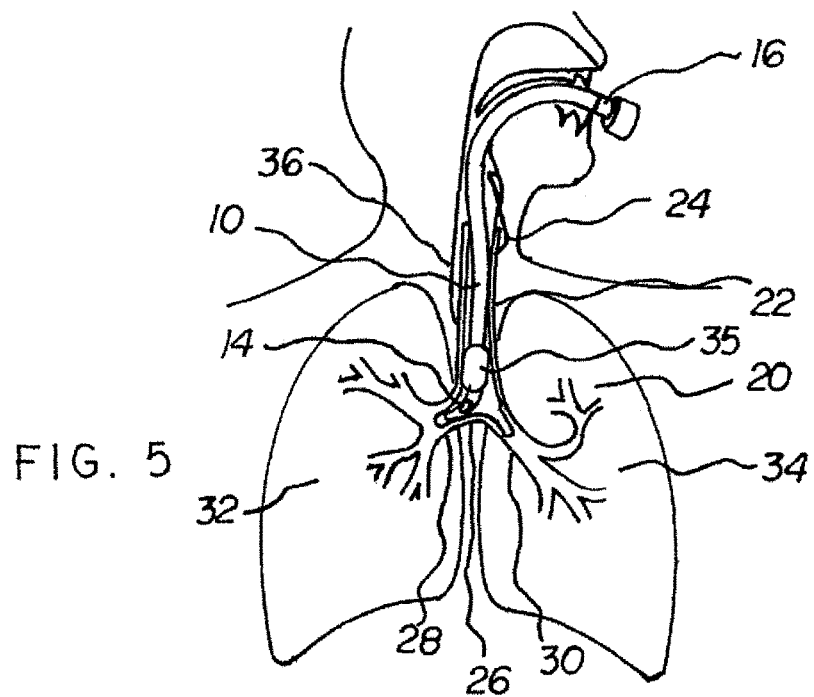
FIG. 5 is a diagrammatical view illustrating improper placement of an ETT past a carina and into a right main bronchus.

Referring now to the drawings, FIGS. 3-5 illustrate insertion of an ETT 10 into a human body 12. ETT 10 includes a hollow tube having a distal end 14 for insertion into body 12 and a connector 16 located outside body 12. Illustratively, ETT 10 is inserted into a mouth 18 of the patient. A respiratory system 20 includes a trachea 22 which extends between vocal folds 24 of a larynx and a first bifurcation known as a carina 26. Airways formed by carina 26 include a right primary bronchus 28 and a left primary bronchus 30. Continuing farther down the airway, bronchial tubes branch into smaller and smaller tubes.

FIG. 3 illustrates proper insertion of ETT 10 into trachea 22 between vocal folds 24 and carina 26. For proper mechanical ventilation of the patient, it is important that distal end 14 of ETT 10 is positioned properly within trachea 22 between vocal folds 24 and carina 26 to provide adequate ventilation to both lungs 32 and 34. An inflatable cuff 35 provides a seal between the ETT 10 and the airway, as described in greater detail hereinbelow.

Insertion of ETT 10 into the trachea 22 is sometimes a difficult procedure. As illustrated in FIG. 4, it is possible for distal end 14 of ETT 10 to miss the entrance to trachea 22 and enter an esophagus 36 leading to the stomach (not shown). Improper placement of ETT 10 into the esophagus is most evident in a pre-hospital or emergency room setting which is characterized by high stress and limited time. Improper placement of open distal end 14 of ETT 10 into the esophagus 36 prevents ventilation of lungs 32 and 34.

Improper insertion of distal end 14 of ETT 10 past carina 26 will result in ventilation of only right lung 32 or left lung 34. FIG. 5 illustrates improper insertion of distal end 14 of ETT 10 past carina 26 and into right main bronchus 28. Because right primary bronchus 28 is shorter, wider, and more vertical than left primary bronchus 30, the majority of ETT insertions past carina 26 tend to follow the right primary bronchus 28. The speaker/microphone guidance systems disclosed in U.S. Pat. Nos. 5,455,144 and 6,705,319 to Wodicka, et at, detect if ETT 10 is improperly inserted into esophagus 36, right primary bronchus 28, or left primary bronchus 30 and alert a user to the improper placement. The apparatus can then be used to guide movement of UT 10 back into its proper position within trachea 22.

Figure 6:
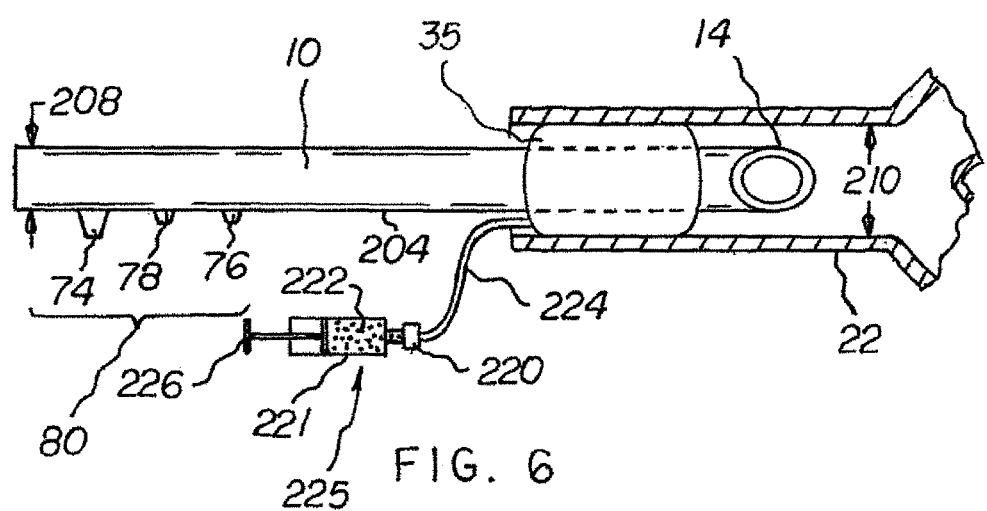
FIG. 6 is a cross-sectional diagrammatical view of one embodiment leak detection system.

According to some embodiments of the present disclosure, the Err 10 may be equipped with a cuff 35 as shown in FIG. 6. The cuff 35, known to a person having ordinary skill in the art, is coupled to a tubular portion 204 of the ETT 10 near the distal end 14. In FIG. 6, the ETT 10 is shown inserted into a body cavity, such as a trachea 22. The cuff 35 is configured to be a flexible member. In one form, the cuff 35 is formed in a substantially toroidal form, having any desired cross-sectional shape such as circular, oval, square or rectangular, to name just a few non-limiting examples. Pressurizing the interior of the cuff 35 with a gas or fluid can adjust an outer diameter (identified by reference numeral 210) of the cuff 35 with respect to an inner diameter (identified by reference numeral 208), thereby determining the pressure with which the cuff 35 presses against both the tubular portion 204 of the ETT 10 and the walls of the trachea 22. The inner portion of the cuff 35 is coupled to the outer surface of the tubular portion 204. The cuff 35 can be permanently coupled to the tubular portion 204, e.g., by being molded to or glued to the tubular portion 204, or in other manners that will be apparent to those skilled in the art in view of the present disclosure.

The cuff 35 may be in communication with an inflation device 225. In one embodiment, the inflation device 225 comprises a one-way valve 220 to which a syringe 221(or other appropriate device) may be attached. The inflation device 225 can be configured to inflate the cuff 35 for an improved sealing against the anatomical conduit such as the trachea 22. Syringe 221 contains a gas or fluid 222 that may be injected to, or withdrawn from, the cuff 35 through the tube 224 by actuation of the plunger 226. Once inflated, the syringe 221 may be optionally disconnected from the one-way valve 220. Other devices known in the art may be used as an inflation device 225, such as a pump, for example.

The cuff 35, when properly pressurized, is configured to prevent backflow of air, or other fluids (e.g., blood, mucous, liquid and gaseous compounds, etc.), collectively referred to hereunder as air or other fluids, between the tubular portion 204 of the ETT 10 and the trachea 22, or other anatomical structures, collectively referred to hereunder as anatomical conduits, with which the ETT 10 or other tubular device is used to transfer air or other fluids therein. Such a backflow is undesired in ventilation and other applications in which the air or other fluids are introduced through the ETT 10 to an anatomical conduit, as it is desired to maintain a positive pressure within the anatomical conduit. In the case of an ETT 10 positioned within a trachea 22, the cuff 35 performs the further function of preventing the flow of accumulated fluids that may be proximal to the cuff 35 past the cuff 35 and into the lungs. Such unintended flow can cause pneumonia in the patient.

The undesirable passage of the air or other fluids between the cuff 35 and the anatomical conduit generates vibrations. The vibrations can generate waves that can be sensed by a detection device that may include the first microphone 76 and/or the second microphone 78. The microphone(s) 76, 78 may be coupled to an external speaker or headphones through an appropriate optional amplifier so that a user can listen for the sound made by the fluid leaking past the cuff 35. In one embodiment, the inflation device 225 is operated to increase the pressure in the cuff 35 until the user detects that the sound generated by the leakage past the cuff 35 has stopped or substantially stopped. An appropriate pressure sensor of the cuff 35 (and/or the inflation device 225) may sense a cuff pressure and record the cuff pressure at this point in time and adjustment of the cuff pressure using the inflation device 225 may be made throughout the remaining time that the ETT 10 is inserted in order to maintain the cuff 35 at that pressure. Such monitoring and maintenance of the appropriate pressure may be done manually by the operator, or under the control of a computer or other processing device as will be appreciated by those skilled in the art in view of the present disclosure. For example, an automated system may be used to maintain the cuff 35 pressure at a set point, and that set point may be determined by acoustic feedback identifying the presence or absence of sound leaking past the cuff 35.

In some embodiments, two microphones (such as those illustrated in FIGS. 2 and 6), may be used in order to help identify the sounds indicative of leakage past the cuff 35. As described hereinabove, two microphones 76, 78 may be used to determine the direction of travel of a sound. Using such techniques, the system may differentiate between sounds that arise from the machine (e.g., ventilator) end from those that arise from the patient end. The system may use this information to verify that the sound identified as noise leaking past the cuff 35 is indeed propagating in a direction coming from the cuff 35 to the microphones 76, 78 using a temporal analysis or other appropriate analysis.

In other embodiments, the cuff 35 can be initially filled to a predetermined pressure (such as a pressure recommended by the manufacturer of the ETT 10). Thereafter, the microphones 76, 78 can be used to monitor for a leak past the cuff 35 and, if detected, the inflation device 225 can be used to increase the pressure in the cuff 35 until the leakage is heard to cease or substantially cease.

In other embodiments, the leak detection may also be automated, with a detection system configured to detect vibrations generated due to the backflow of the air or other fluids. In other embodiments, the processor may have direct control of the operation of the inflation device 225 and can automatically adjust the pressure in the cuff 202.

Figure 7:
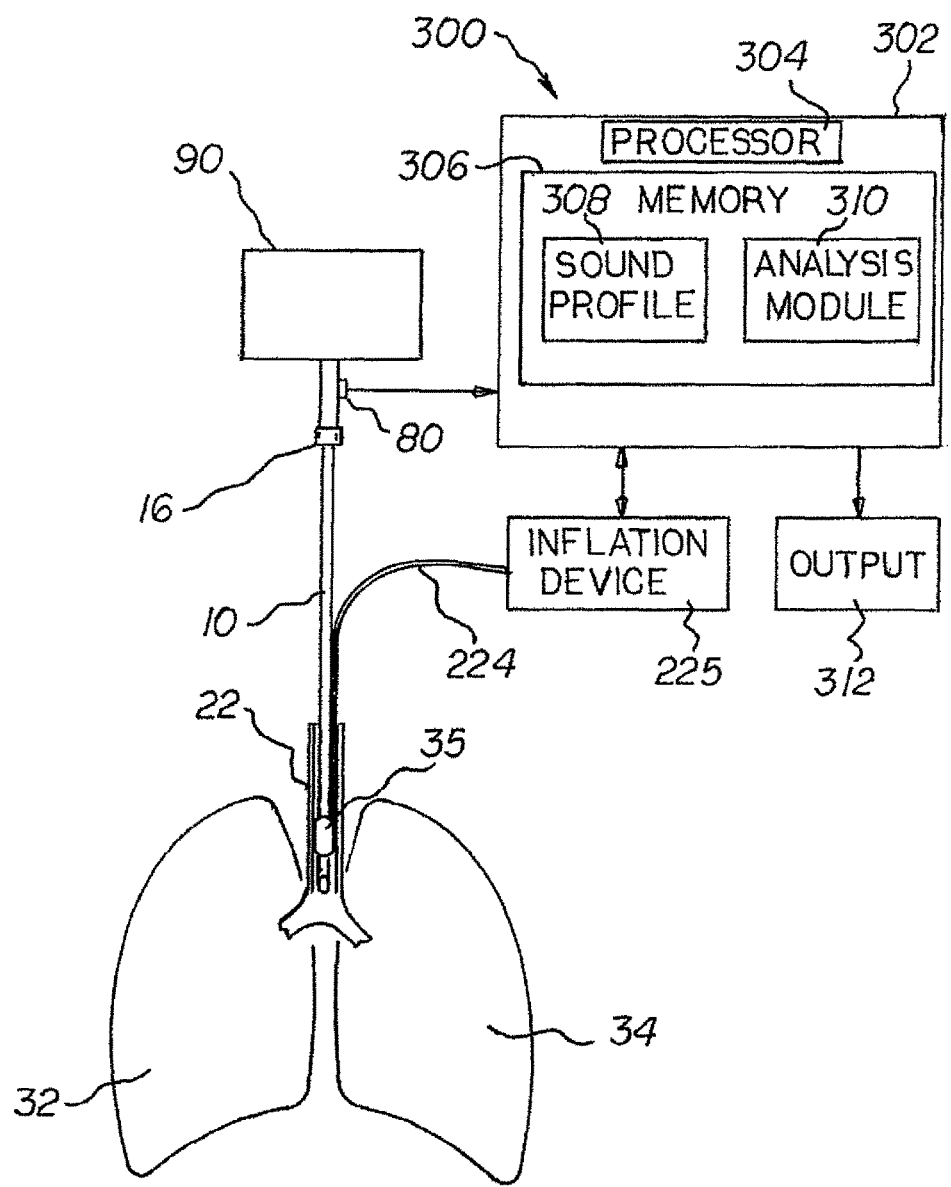
FIG. 7 is a diagrammatical view of a particular illustrative embodiment of a leak detection method for tube or catheter placement.

Referring to FIG. 7, a particular illustrative embodiment of a leak detection system is depicted and generally designated 300. As described above, the ETT 10 may be inserted into the anatomical conduit, such as a trachea 22 and equipped with a cuff 35. The pressure of the cuff 35 can be increased and decreased to adjust to an outer diameter of the cuff 35 to press against the ETT 10 and the walls of the trachea 22. The system 300 includes a processor 304 that is communication with a vibration detection device 80 configured to detect acoustic waves generated by vibrations caused by a leak of fluids between the cuff 35 and an anatomical conduit 22. In addition, the tube 10 may be adapted to be coupled via connector 16 to a medical device 90, such as a mechanical ventilator, a breathing bag, an anesthesia machine, or an infusion pump. A memory 306 of a computer 302 may be configured to store baseline expected sound profile(s) 308. An analysis module 310 may be used to determine whether signals received from the microphones 76, 78 of the vibration detection device 80 indicate a leak around the cuff 35 when compared to the expected sound profiles 308. In addition, an output device 312 may be in direct communication with the computer 302, where the output device 312 is able to render an audio alert, visual alert, or any combination thereof. For example, a cathode ray tube (CRT) display, liquid crystal display (LCD), light emitting diode (LED) display, plasma display, or other display device that is accessible to the processor 304 to display a visual rendering of the expected sound profiles 308 and the signals received from the microphones 76, 78.

An inflation device 225 may be in communication with the cuff 35 via tube 224 and the computer 302. The sound profile(s) 308 and analysis module 310 may be implemented in hardware, firmware, software, other programmable logic, or any combination thereof. The memory 306 includes media that is readable by the processor 304 and that stores data and program instructions that are executable by the processor 304.

In operation, the sound profile exhibited by air or other fluids leaking past the cuff 35 may be characterized, such as vibrations within a defined frequency range detected over a minimum window of time. The processor 302 of the detection system 300 is programmed to analyze the signals generated by one or more microphones 76, 78 of the vibration detection device 80, and to detect a sound pattern matching the known leakage sound profile 308. In an alternative embodiment, a baseline is established for normal passage of the air or other fluids, i.e., absence of a backflow of the air or other fluids caused by leakage past the cuff 35, and a processor 304 of the detection system 300 is programmed to analyze signals generated by at least one the microphone 76 or 78. The processor 304 can then be programmed to recognize vibrations caused due to the backflow of the air or other fluids, such vibrations being in addition to the expected baseline vibrations. When the processor 304 identifies the air or other fluids are leaking due to the backflow, the processor 304 can then provide an audio and/or visual alert to an operator to take corrective actions.

Figure 8:
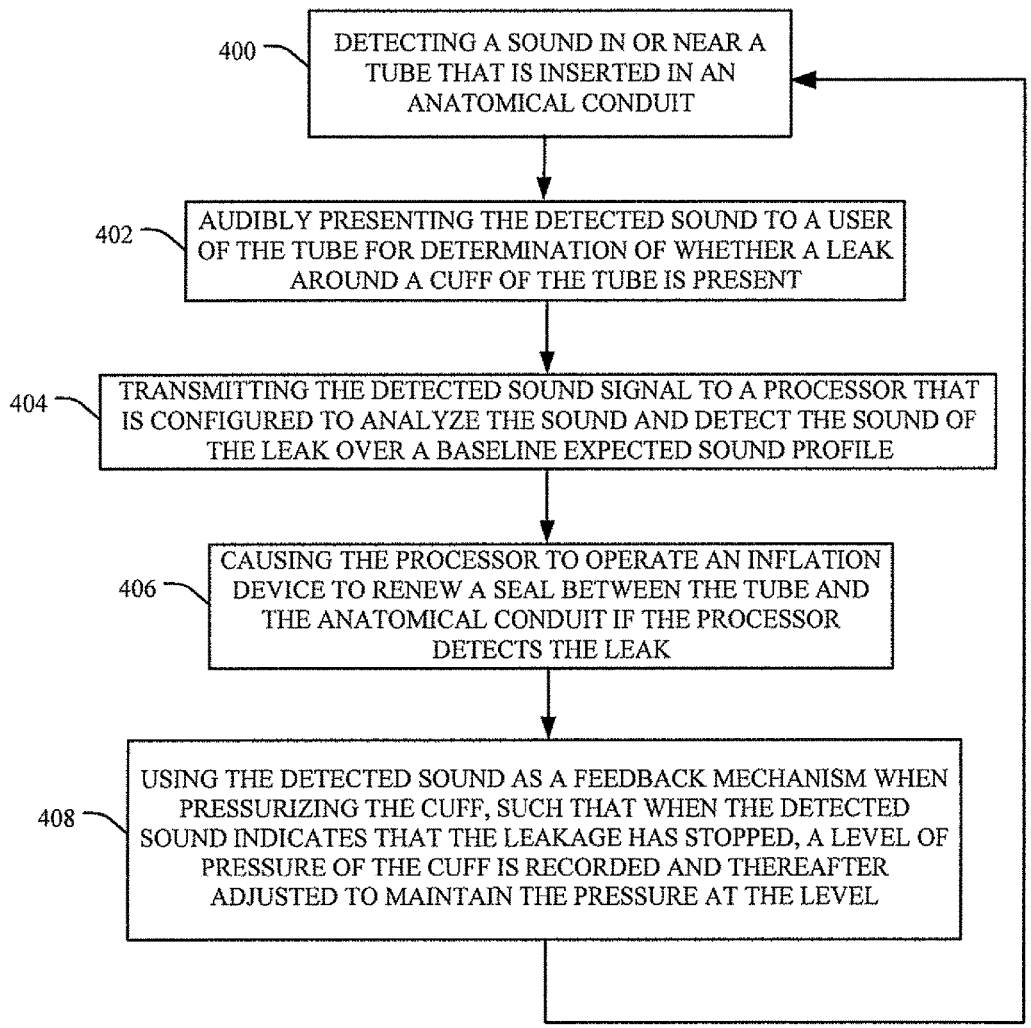
FIG. 8 is a flow diagram of a particular embodiment of a leak detection method for placement of a tube or catheter.

A flow diagram of a particular embodiment of a leak detection method is described in FIG. 8. At 400, a sound in or near a tube that is inserted in an anatomical conduit is detected using a microphone. The sound may be generated from a speaker within the tube or acoustic waves generated by vibrations caused by a leak of fluids between a cuff and an anatomical conduit. Moving to 402, the detected sound may be audibly presented to an operator of the tube for determination of whether a leak around a cuff of the tube is present. In addition, or alternatively, the detected sound signal may be transmitted, at 404, to a processor that is configured to analyze the sound and detect the sound of the leak over a baseline expected sound profile. The processor is configured to operate and cause an inflation device to renew a seal between the tube and the anatomical conduit if the processor detects the leak, at 406. The detected sound may be used as a feedback mechanism when pressurizing the cuff, at 408, such that when the detected sound indicates that the leakage has stopped, a level of pressure of the cuff is recorded and thereafter adjusted to maintain the pressure at the level.

Although the system and method described is related to maintaining a seal around an ETT 10 within a respiratory system of a body, it is understood that the system and method of the present disclosure may be used to maintain seals around gas or liquid filled tubes or catheters into other body cavities or in various mechanical operations. The leak detection system and method can be applied to a wide variety of clinical tubes or catheters where maintenance of a seal therearound is required.

Although the teachings of the present disclosure have been described in detail with reference to certain embodiments, variations and modifications exist within the scope and spirit of these teaching as described and defined in the following claims:

What is claimed is:

1. A leak detection system for tube placement, the system comprising:
   a tube;
   an inflatable cuff coupled to the tube;
   a microphone at only one location coupled to the tube and configured to detect acoustic waves generated by vibrations from a passage of air between the inflatable cuff and an anatomical conduit when inserted in the anatomical conduit; and
   a microprocessor having a memory and the microprocessor coupled to the microphone and configured to compare the acoustic waves to a baseline expected sound profile stored in the memory and determine that a leak around the inflatable cuff is present when the acoustic waves are in addition to the expected sound profile, the baseline expected profile is established by detection of a frequency range over a duration of time, such that the expected baseline sound profile defines an absence of a backflow of the air and other fluids caused by leakage past the cuff.

2. The leak detection system of claim 1, further comprising an inflation device coupled to the inflatable cuff, wherein the inflation device is configured to increase a pressure in the inflatable cuff when leakage is detected to renew a seal between the inflatable cuff and the anatomical conduit.

3. The leak detection system of claim 1, further comprising a pressure sensor in communication with the inflatable cuff.

4. The leak detection system of claim 2, wherein the inflation device is coupled to the microprocessor and configured to automatically activate the inflation device to increase the pressure in the inflatable cuff when leakage is detected.

5. The leak detection system of claim 2, wherein the microprocessor is configured to generate an alert when leakage is detected.

6. The leak detection system of claim 3, further comprising an external speaker coupled to the microphone.

7. The leak detection system of claim 4, further comprising a display configured to visually display at least one baseline expected sound profile stored in the memory and the detected acoustic waves from the microphone.

8. The leak detection system of claim 5, wherein the tube comprises a catheter.

9. The leak detection system of claim 1, wherein the inflatable cuff is coupled to a periphery of a distal end of the tube.

10. A leak detection system for tube placement, the system comprising:
    a tube;
    an inflatable cuff coupled to the tube;
    a microphone at only one location configured to detect acoustic waves generated by vibrations from a passage of air between the inflatable cuff and an anatomical conduit;
    a microprocessor having a memory and the microprocessor coupled to the microphone and configured to compare the acoustic waves to a baseline expected sound profile stored in the memory and determine that a leak around the inflatable cuff is present when the acoustic waves are in addition to the expected sound profile, the baseline expected profile is established by detection of a frequency range over a duration of time, such that the expected baseline sound profile defines an absence of a backflow of the air and other fluids caused by leakage past the cuff; and
    an inflation device coupled to the inflatable cuff.

11. The leak detection device of claim 10, further comprising a mechanical ventilator coupled to the tube.

12. The leak detection device of claim 10, wherein the anatomical conduit comprises a trachea.

13. The leak detection system of claim 10, wherein the inflation device is configured to increase a pressure in the inflatable cuff when leakage is detected.

14. The leak detection system of claim 10, wherein the inflation device comprises a pump.

15. The leak detection system of claim 10, further comprising a pressure sensor in communication with the inflatable cuff.

16. The leak detection system of claim 10, wherein the inflation device is coupled to the microprocessor and configured to automatically activate the inflation device to increase the pressure in the inflatable cuff when leakage is detected.

17. The leak detection system of claim 10, wherein the microprocessor is configured to generate an alert when leakage is detected.

18. The leak detection system of claim 10, further comprising an external speaker coupled to the microphone.

19. The leak detection system of claim 10, further comprising a display configured to visually display at least one baseline expected sound profile and the detected acoustic waves from the microphone.

20. The leak detection system of claim 10, wherein the tube comprises a catheter.

* * * * *